(12) United States Patent
Chen et al.

(10) Patent No.: US 11,169,248 B2
(45) Date of Patent: Nov. 9, 2021

(54) MULTI-LEVEL PULSER AND RELATED APPARATUS AND METHODS

(71) Applicant: BFLY Operations, Inc., Guilford, CT (US)

(72) Inventors: Kailiang Chen, Branford, CT (US); Tyler S. Ralston, Clinton, CT (US)

(73) Assignee: BFLY Operations, Inc., Guilford, CT (US)

( * ) Notice: Subject to any disclaimer, the term of this patent is extended or adjusted under 35 U.S.C. 154(b) by 697 days.

(21) Appl. No.: 15/934,150

(22) Filed: Mar. 23, 2018

(65) Prior Publication Data
US 2018/0210073 A1    Jul. 26, 2018

Related U.S. Application Data

(63) Continuation of application No. 15/645,771, filed on Jul. 10, 2017, now Pat. No. 9,958,537, which is a
(Continued)

(51) Int. Cl.
*G01S 7/524*    (2006.01)
*A61B 8/00*    (2006.01)
(Continued)

(52) U.S. Cl.
CPC .......... *G01S 7/524* (2013.01); *A61B 8/4483* (2013.01); *A61B 8/54* (2013.01); *G01S 7/521* (2013.01);
(Continued)

(58) Field of Classification Search
CPC ........ G01S 7/521; G01S 7/524; G01S 7/5208; G01S 7/5202; G01S 7/52096;
(Continued)

(56) References Cited

U.S. PATENT DOCUMENTS 3,274,821 A    9/1966    Weighart
3,367,173 A    2/1968    Uphoff
(Continued)

FOREIGN PATENT DOCUMENTS

CN    1279844 A    1/2001
CN    1414384 A    4/2003
(Continued)

OTHER PUBLICATIONS

Invitation to Pay Additional Fees dated Jan. 17, 2017 for Application No. PCT/US2016/064421.
(Continued)

*Primary Examiner* — Oommen Jacob
(74) *Attorney, Agent, or Firm* — Wolf, Greenfield & Sacks, P.C.

(57) ABSTRACT

Apparatus and methods are provided directed to a device, including at least one ultrasonic transducer, a multi-level pulser coupled to the at least one ultrasonic transducer; the multi-level pulser including a plurality of input terminals configured to receive respective input voltages, an output terminal configured to provide an output voltage, and a signal path between a first input terminal and the output terminal including a first transistor having a first conductivity type coupled to a first diode and, in parallel, a second transistor having a second conductivity type coupled to a second diode.

10 Claims, 5 Drawing Sheets

Related U.S. Application Data continuation of application No. 15/288,324, filed on Oct. 7, 2016, now Pat. No. 9,933,516, which is a continuation of application No. 14/957,382, filed on Dec. 2, 2015, now Pat. No. 9,492,144.

(51) Int. Cl.
  *G01S 7/52* (2006.01)
  *G01S 7/521* (2006.01)
  *H03K 19/0175* (2006.01)

(52) U.S. Cl.
  CPC .......... *G01S 7/5202* (2013.01); *G01S 7/5208* (2013.01); *G01S 7/52096* (2013.01); *H03K 19/017545* (2013.01)

(58) Field of Classification Search
  CPC ......... A61B 8/4483; A61B 8/54; H03K 19/017545; H03K 19/00–0002; H03K 19/018521–018528
  See application file for complete search history.

(56) References Cited

U.S. PATENT DOCUMENTS

| | | | |
|---|---|---|---|
| 3,787,803 A | 1/1974 | Beebe | |
| 4,098,130 A | 7/1978 | Coffey et al. | |
| 4,464,587 A * | 8/1984 | Suzuki | H03K 3/3565 327/206 |
| 4,504,747 A * | 3/1985 | Smith | H03K 19/018521 326/70 |
| 4,512,350 A | 4/1985 | Cimilluca | |
| 4,783,819 A | 11/1988 | De Koning et al. | |
| 4,793,825 A | 12/1988 | Benjamin et al. | |
| 5,057,719 A | 10/1991 | Niedra | |
| 5,622,177 A * | 4/1997 | Breimesser | G01S 15/8925 600/459 |
| 5,831,470 A * | 11/1998 | Park | H02M 3/073 327/536 |
| 5,844,445 A | 12/1998 | Takeyari | |
| 6,208,189 B1 | 3/2001 | Freeman et al. | |
| 6,525,949 B1 * | 2/2003 | Johnson | H02M 3/073 363/60 |
| 6,530,887 B1 * | 3/2003 | Gilbert | G01S 7/52025 600/459 |
| 6,600,679 B2 * | 7/2003 | Tanzawa | G11C 16/30 365/189.11 |
| 7,176,720 B1 * | 2/2007 | Prather | H03K 19/018528 326/80 |
| 7,256,654 B2 | 8/2007 | White et al. | |
| 7,313,053 B2 | 12/2007 | Wodnicki | |
| 7,411,439 B2 * | 8/2008 | Brox | H03K 19/018521 326/62 |
| 7,564,263 B2 * | 7/2009 | Walker | H03K 3/356113 326/63 |
| 8,089,309 B2 | 1/2012 | Jansen et al. | |
| 8,143,924 B2 * | 3/2012 | Hanazawa | H03K 17/74 327/108 |
| 8,525,570 B2 | 9/2013 | Ha et al. | |
| 8,766,721 B1 | 7/2014 | Dusad | |
| 8,852,103 B2 | 10/2014 | Rothberg et al. | |
| 9,112,521 B2 | 8/2015 | Dedic et al. | |
| 9,197,200 B2 * | 11/2015 | Teplechuk | H03K 3/356182 |
| 9,229,097 B2 | 1/2016 | Rothberg et al. | |
| 9,270,273 B2 * | 2/2016 | Mukhopadhyay | H03K 19/018507 |
| 9,473,116 B1 * | 10/2016 | Wang | H03K 3/037 |
| 9,473,136 B1 | 10/2016 | Chen et al. | |
| 9,492,144 B1 | 11/2016 | Chen et al. | |
| 9,705,518 B2 | 7/2017 | Chen et al. | |
| 9,933,516 B2 | 4/2018 | Chen et al. | |
| 9,958,537 B2 | 5/2018 | Chen et al. | |
| 10,014,871 B2 | 7/2018 | Chen et al. | |
| 10,082,488 B2 | 9/2018 | Chen et al. | |
| 10,082,565 B2 * | 9/2018 | Chen | G01S 15/8915 |
| 10,175,347 B2 | 1/2019 | Chen et al. | |
| 10,187,020 B2 | 1/2019 | Chen et al. | |
| 10,277,236 B2 | 4/2019 | Chen et al. | |
| 10,478,154 B2 * | 11/2019 | Brown | G10K 11/346 |
| 10,624,613 B2 | 4/2020 | Ralston | |
| 10,707,886 B2 | 7/2020 | Chen et al. | |
| 10,820,888 B2 * | 11/2020 | Boser | B06B 1/0662 |
| 2002/0039042 A1 * | 4/2002 | Jinzai | H03K 19/018521 327/333 |
| 2002/0045818 A1 | 4/2002 | Jeon | |
| 2003/0107422 A1 * | 6/2003 | Miyagi | H03K 17/223 327/215 |
| 2003/0158478 A1 | 8/2003 | Petersen et al. | |
| 2003/0173644 A1 * | 9/2003 | Nakase | H03K 17/102 257/532 |
| 2004/0100318 A1 * | 5/2004 | Lim | H03K 19/018521 327/333 |
| 2005/0154300 A1 | 7/2005 | Wodnicki et al. | |
| 2005/0203392 A1 | 9/2005 | Petersen et al. | |
| 2005/0206412 A1 | 9/2005 | Moraveji | |
| 2005/0248558 A1 | 11/2005 | Kobashi | |
| 2006/0058588 A1 | 3/2006 | Zdeblick | |
| 2006/0061386 A1 * | 3/2006 | Kanzaki | H03K 19/018521 326/81 |
| 2006/0209632 A1 | 9/2006 | Goodman et al. | |
| 2007/0001764 A1 | 1/2007 | Huang et al. | |
| 2007/0014190 A1 | 1/2007 | Fehl et al. | |
| 2007/0242567 A1 | 10/2007 | Daft et al. | |
| 2008/0021327 A1 * | 1/2008 | El-Bialy | A61N 7/00 600/459 |
| 2008/0088341 A1 * | 4/2008 | Kimura | H03K 19/018528 326/80 |
| 2008/0225639 A1 * | 9/2008 | Hongou | G01S 7/52052 367/13 |
| 2008/0238532 A1 * | 10/2008 | Hanazawa | H03K 19/018521 327/534 |
| 2008/0264171 A1 | 10/2008 | Wodnicki | |
| 2008/0269614 A1 | 10/2008 | Adachi et al. | |
| 2008/0309395 A1 * | 12/2008 | Kaneko | H03K 19/01812 327/333 |
| 2009/0140810 A1 | 6/2009 | Kim et al. | |
| 2009/0250729 A1 | 10/2009 | Lemmerhirt et al. | |
| 2009/0289716 A1 | 11/2009 | Jaeger et al. | |
| 2010/0026343 A1 * | 2/2010 | Yang | H03K 19/018521 326/80 |
| 2010/0041997 A1 | 2/2010 | Amemiya et al. | |
| 2010/0152587 A1 | 6/2010 | Haider et al. | |
| 2010/0231259 A1 * | 9/2010 | Jung | H03K 19/018521 326/81 |
| 2010/0317972 A1 | 12/2010 | Baumgartner et al. | |
| 2011/0028845 A1 * | 2/2011 | Haider | A61B 8/4483 600/459 |
| 2011/0043269 A1 * | 2/2011 | Nishijima | H03K 19/018521 327/333 |
| 2011/0051536 A1 * | 3/2011 | Park | G11C 7/222 365/194 |
| 2011/0285457 A1 | 11/2011 | Ko et al. | |
| 2012/0262221 A1 | 10/2012 | Bottarel et al. | |
| 2013/0106485 A1 * | 5/2013 | Mukhopadhyay | H03K 19/018507 327/333 |
| 2013/0187697 A1 | 7/2013 | Choy et al. | |
| 2013/0314154 A1 | 11/2013 | Yoshikawa | |
| 2014/0078866 A1 | 3/2014 | Kanamori et al. | |
| 2014/0152369 A1 * | 6/2014 | Qi | H03K 19/018521 327/333 |
| 2014/0288428 A1 | 9/2014 | Rothberg et al. | |
| 2014/0296687 A1 | 10/2014 | Irazoqui et al. | |
| 2014/0340136 A1 * | 11/2014 | Teplechuk | H03K 19/018592 327/333 |
| 2015/0032002 A1 | 1/2015 | Rothberg et al. | |
| 2015/0078125 A1 | 3/2015 | Falter et al. | |
| 2015/0123640 A1 * | 5/2015 | Kondou | H02M 1/088 323/299 |
| 2015/0297193 A1 | 10/2015 | Rothberg et al. | |

(56) References Cited

U.S. PATENT DOCUMENTS

| | | | |
|---|---|---|---|
| 2015/0374335 A1* | 12/2015 | Brown | G01S 15/8993 600/447 |
| 2017/0160239 A1 | 6/2017 | Chen et al. | |
| 2017/0160387 A1 | 6/2017 | Chen et al. | |
| 2017/0160388 A1 | 6/2017 | Chen et al. | |
| 2017/0163225 A1 | 6/2017 | Chen et al. | |
| 2017/0163276 A1 | 6/2017 | Chen et al. | |
| 2017/0202541 A1 | 7/2017 | Ralston | |
| 2017/0264307 A1 | 9/2017 | Chen et al. | |
| 2017/0307739 A1 | 10/2017 | Chen et al. | |
| 2018/0210073 A1* | 7/2018 | Chen | G01S 7/52096 |
| 2018/0262200 A1 | 9/2018 | Chen et al. | |
| 2018/0364200 A1 | 12/2018 | Chen et al. | |
| 2019/0086525 A1 | 3/2019 | Chen et al. | |
| 2019/0140603 A1 | 5/2019 | Chen et al. | |
| 2019/0253061 A1 | 8/2019 | Chen et al. | |
| 2019/0336111 A1 | 11/2019 | Chen et al. | |
| 2020/0150252 A1 | 5/2020 | Chen et al. | |

FOREIGN PATENT DOCUMENTS

| | | |
|---|---|---|
| CN | 1439461 A | 9/2003 |
| CN | 1564462 A | 1/2005 |
| CN | 1694140 A | 11/2005 |
| CN | 101040440 A | 9/2007 |
| CN | 101144797 A | 3/2008 |
| CN | 101176674 A | 5/2008 |
| CN | 100579458 C | 1/2010 |
| CN | 101647714 A | 2/2010 |
| CN | 101809461 A | 8/2010 |
| CN | 101904751 A | 12/2010 |
| CN | 102481139 A | 5/2012 |
| CN | 103033816 A | 4/2013 |
| CN | 103250117 A | 8/2013 |
| CN | 103607130 A | 2/2014 |
| CN | 103795363 A | 5/2014 |
| CN | 104054120 A | 9/2014 |
| CN | 104579256 A | 4/2015 |
| CN | 104638962 A | 5/2015 |
| CN | 104813404 A | 7/2015 |
| CN | 108472008 A | 8/2018 |
| EP | 1 932 479 A1 | 6/2008 |
| EP | 3383278 A | 10/2018 |
| EP | 3454082 A1 | 3/2019 |
| FR | 2 726 408 A1 | 5/1996 |
| JP | 04-062494 | 2/1992 |
| JP | H06-085585 A | 3/1994 |
| JP | H08257019 A | 10/1996 |
| JP | H11-261764 A | 9/1999 |
| JP | 2002-125969 A | 5/2002 |
| JP | 2002263104 A | 9/2002 |
| JP | 2006-061695 A | 3/2006 |
| JP | 2007111257 A | 5/2007 |
| JP | 2008-042521 A | 2/2008 |
| JP | 2009142352 A | 7/2009 |
| JP | 2010-022761 A | 2/2010 |
| JP | 2010-034855 A | 2/2010 |
| JP | 2010-042146 A | 2/2010 |
| JP | 2010-167167 A | 8/2010 |
| JP | 2010-193329 A | 9/2010 |
| JP | 2012-060328 A | 3/2012 |
| JP | 2012-528685 A | 11/2012 |
| JP | 2013-247536 A | 12/2013 |
| JP | 2014-198234 A | 10/2014 |
| JP | 2014-204195 A | 10/2014 |
| JP | 2015-033123 A | 2/2015 |
| JP | 2015-056890 A | 3/2015 |
| JP | 2015-115883 A | 6/2015 |
| JP | 2006-345481 A | 12/2016 |
| JP | 2018537185 A | 12/2018 |
| KR | 10-1024849 B1 | 3/2011 |
| TW | 201445554 A | 12/2014 |
| WO | WO 2010/055427 A1 | 5/2010 |
| WO | 2017/096033 A1 | 6/2017 |
| WO | 2017/096043 A1 | 6/2017 |

OTHER PUBLICATIONS

International Search Report and Written Opinion dated Apr. 4, 2017 for Application No. PCT/US2016/064421.

Taiwanese Office Action dated Jan. 19, 2018 in connection with Taiwanese Application No. 105139662.

Agarwal et al., Single-Chip Solution for Ultrasound Imaging Systems: Initial Results. 2007 IEEE Ultrasonics Symposium. Oct. 1, 2007;1563-6.

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of A Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

International Preliminary Report on Patentability dated Jun. 14, 2018 in connection with International Application No. PCT/US2016/064421.

Extended European Search Report dated Jun. 18, 2019 in connection with European Application No. 16871486.3.

Extended European Search Report dated Jul. 18, 2019 in connection with European Application No. 16871492.1.

Extended European Search Report dated Jun. 17, 2019 in connection with European Application No. 16871500.1.

Extended European Search Report dated May 28, 2019 in connection with European Application No. 16871466.5.

Extended European Search Report dated Jun. 4, 2019 in connection with European Application No. 16871463.2.

Reyes et al., A 2GS/s 6-bit CMOS time-interleaved ADC for analysis of mixed-signal calibration techniques. Analog Integrated Circuits and Signal Processing. Springer New York LLC. Jul. 3, 2015; 85(1):3-16.

Um et al., 24.8 An Analog-digital-hybrid single-chip RX beamformer with non-uniform sampling for 2D-CMUT ultrasound imaging to achieve wide dynamic range of delay and small chip area. IEEE International Solid State Circuits Conference. IEEE Service Center. Feb. 9, 2014; pp. 427-437.

EP 16871486.3, Jun. 18, 2019, Extended European Search Report.
EP 16871492.1, Jul. 18, 2019, Extended European Search Report.
EP 16871500.1, Jun. 17, 2019, Extended European Search Report.
EP 16871466.5, May 28, 2019, Extended European Search Report.
EP 16871463.2, Jun. 4, 2019, Extended European Search Report.

(56) References Cited

OTHER PUBLICATIONS

Chinese First Office Action dated Jul. 3, 2020 and English translation thereof in connection with Chinese Application No. 201680070793.1.
International Search Report and Written Opinion dated Jan. 29, 2020 for Application No. PCT/US2019/060399.
EP 18201497.7, dated Feb. 13, 2019, Extended European Search Report.
Extended European Search Report dated Feb. 13, 2019 in connection with European Application No. 18201497.7.
European Communication dated Jun. 25, 2021 in connection with European Application No. 18201497.7.

* cited by examiner

MULTI-LEVEL PULSER AND RELATED APPARATUS AND METHODS

RELATED APPLICATIONS

This Application is a continuation, claiming the benefit under 35 U.S.C. § 120, of U.S. patent application Ser. No. 15/645,771, filed Jul. 10, 2017, entitled "MULTI-LEVEL PULSER AND RELATED APPARATUS AND METHODS" which is hereby incorporated herein by reference in its entirety.

U.S. patent application Ser. No. 15/645,711 is a continuation, claiming the benefit under 35 U.S.C. § 120, of U.S. patent application Ser. No. 15/288,324, filed Oct. 7, 2016, entitled "MULTI-LEVEL PULSER AND RELATED APPARATUS AND METHODS" which is hereby incorporated herein by reference in its entirety.

U.S. patent application Ser. No. 15/288,324 is a continuation, claiming the benefit under 35 U.S.C. § 120, of U.S. patent application Ser. No. 14/957,382, entitled "MULTI-LEVEL PULSER AND RELATED APPARATUS AND METHODS" filed on Dec. 2, 2015, which is hereby incorporated herein by reference in its entirety.

BACKGROUND

Field

The present application relates to ultrasound devices having a multi-level pulser and/or a level shifter.

Related Art

Ultrasound devices may be used to perform diagnostic imaging and/or treatment. Ultrasound imaging may be used to see internal soft tissue body structures. Ultrasound imaging may be used to find a source of a disease or to exclude any pathology. Ultrasound devices use sound waves with frequencies which are higher than those audible to humans. Ultrasonic images are made by sending pulses of ultrasound into tissue using a probe. The sound waves are reflected off the tissue, with different tissues reflecting varying degrees of sound. These reflected sound waves may be recorded and displayed as an image to the operator. The strength (amplitude) of the sound signal and the time it takes for the wave to travel through the body provide information used to produce an image.

Many different types of images can be formed using ultrasound devices. The images can be real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to aspects of the present application, there are provided apparatus and methods directed to an apparatus, including at least one ultrasonic transducer, a multi-level pulser coupled to the at least one ultrasonic transducer; the multi-level pulser including a plurality of input terminals configured to receive respective input voltages, an output terminal configured to provide an output voltage, and a signal path between a first input terminal and the output terminal including a first transistor having a first conductivity type coupled to a first diode and, in parallel, a second transistor having a second conductivity type coupled to a second diode.

According to aspects of the present application, there are provided apparatus and methods directed to a multi-level pulser, including a plurality of input terminals configured to receive respective input voltages, an output terminal configured to provide an output voltage, and a signal path between a first input terminal and the output terminal including a transistor having a first conductivity type coupled to a first diode and, in parallel, a transistor having a second conductivity type coupled to a second diode.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

The inventors have recognized and appreciated that the power necessary to transmit high-intensity pulses may be greatly decreased by forming electric pulses having multiple levels.

Aspects of the present application relate to high-intensity focused ultrasound (HIFU) procedures that may be used to focus high-intensity ultrasound energy on targets to treat diseases or damaged tissues by selectively increasing the temperature of the target or the region surrounding the target. HIFU procedures may be used for therapeutic or ablative purposes. Pulsed signals may be used to generate HIFUs. According to aspects of the present application, the generation of such high-intensity pulses may require driving voltages of several tens to several hundreds of volts.

The power consumption associated with the generation of typical 2-level pulses having a "low" voltage and a "high" voltage is proportional to the square of the high voltage. For example, the generation of a 2-level pulse having a "low" voltage equal to 0 requires a power equal to:

$$P_{(2)} = C*V^2*f$$

where $P_{(2)}$ is the power needed to generate the 2-level pulse, C is the capacitance of the load receiving the pulse, V is the "high" voltage and f is the repetition frequency of the 2-level pulse.

According to aspects of the present application, the power consumption associated with the generation of pulses for HIFU procedures may exceed several tens to thousands of watts, thus causing the circuit to generate significant amounts of heat.

Aspects of the present application relate to multi-level pulsers designed to decrease power consumption and heat dissipation.

Furthermore, aspects of the present application relate to a level shifter circuit configured to drive the multi-level pulser. The level shifter disclosed herein may dissipate considerably less power compared to typical level shifters. Accordingly, power may be dissipated only when a level is switched, while static power consumption may be negligible.

The aspects and embodiments described above, as well as additional aspects and embodiments, are described further below. These aspects and/or embodiments may be used individually, all together, or in any combination of two or more, as the application is not limited in this respect.

Figure 1:
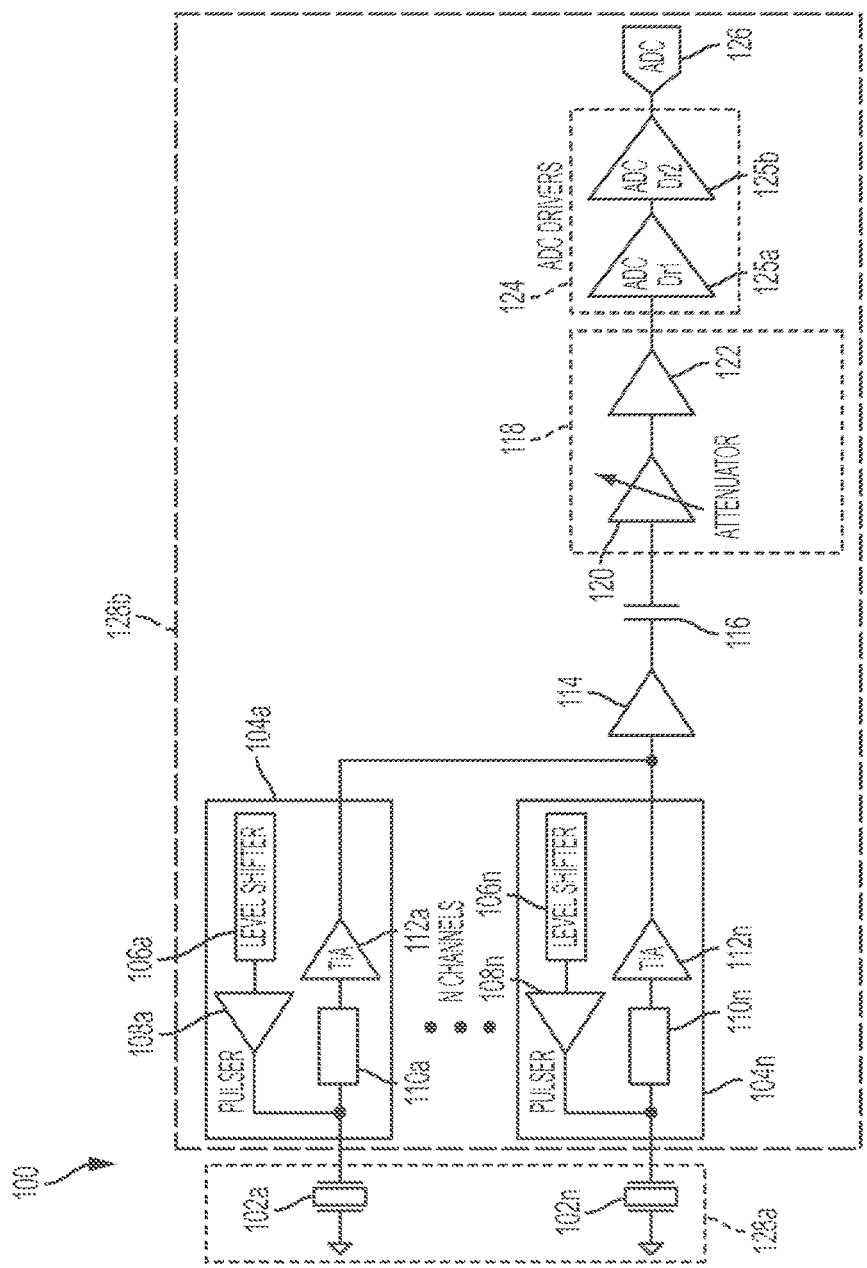
FIG. 1 is a block diagram of an ultrasound device including a multi-level pulser and/or a level shifter, according to a non-limiting embodiment of the present application.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Further alternative types of ultrasonic transducers may be used in other embodiments.

The circuit 100 further comprises N circuitry channels 104a . . . 104n. The circuitry channels may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels.

According to aspects of the present application, the circuitry channels 104a . . . 104n may include transmit circuitry. The transmit circuitry may include level shifters 106a . . . 106n coupled to respective multi-level pulsers 108a . . . 108n. The multi-level pulsers 108a . . . 108n may control the respective ultrasonic transducers 102a . . . 102n to emit ultrasound signals.

Circuitry channels 104a . . . 104n may also include receive circuitry. The receive circuitry of the circuitry channels 104a . . . 104n may receive the electrical signals output from respective ultrasonic transducers 102a . . . 102n. In the illustrated example, each circuitry channel 104a . . . 104n includes a respective receive switch 110a . . . 110n and an amplifier 112a . . . 112n. The receive switches 110a . . . 110n may be controlled to activate/deactivate readout of an electrical signal from a given ultrasonic transducer 102a . . . 102n. More generally, the receive switches 110a . . . 110n may be receive circuits, since alternatives to a switch may be employed to perform the same function. The amplifiers 112a . . . 112n may be trans-impedance amplifiers (TIAs).

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n. The averaging circuit 114 may include a variable feedback resistance. The value of the variable feedback resistance may be adjusted dynamically based upon the number of amplifiers 112a . . . 112n from which the averaging circuit receives signals. The averaging circuit 114 is coupled to an auto-zero block 116.

The auto-zero block 116 is coupled to a time gain compensation circuit 118 which includes an attenuator 120 and a fixed gain amplifier 122. Time gain compensation circuit 118 is coupled to an analog-to-digital converter (ADC) 126 via ADC drivers 124. In the illustrated example, the ADC drivers 124 include a first ADC driver 125a and a second ADC driver 125b. The ADC 126 digitizes the signal(s) from the averaging circuit 114.

While FIG. 1 illustrates a number of components as part of a circuit of an ultrasound device, it should be appreciated that the various aspects described herein are not limited to the exact components or configuration of components illustrated. For example, aspects of the present application relate to the multi-level pulsers 108a . . . 108n and the level shifters 106a . . . 106n.

The components of FIG. 1 may be located on a single substrate or on different substrates. For example, as illustrated, the ultrasonic transducers 102a . . . 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a . . . 102n and the illustrated circuitry may be monolithically integrated on the same semiconductor die. Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient.

Figure 2:
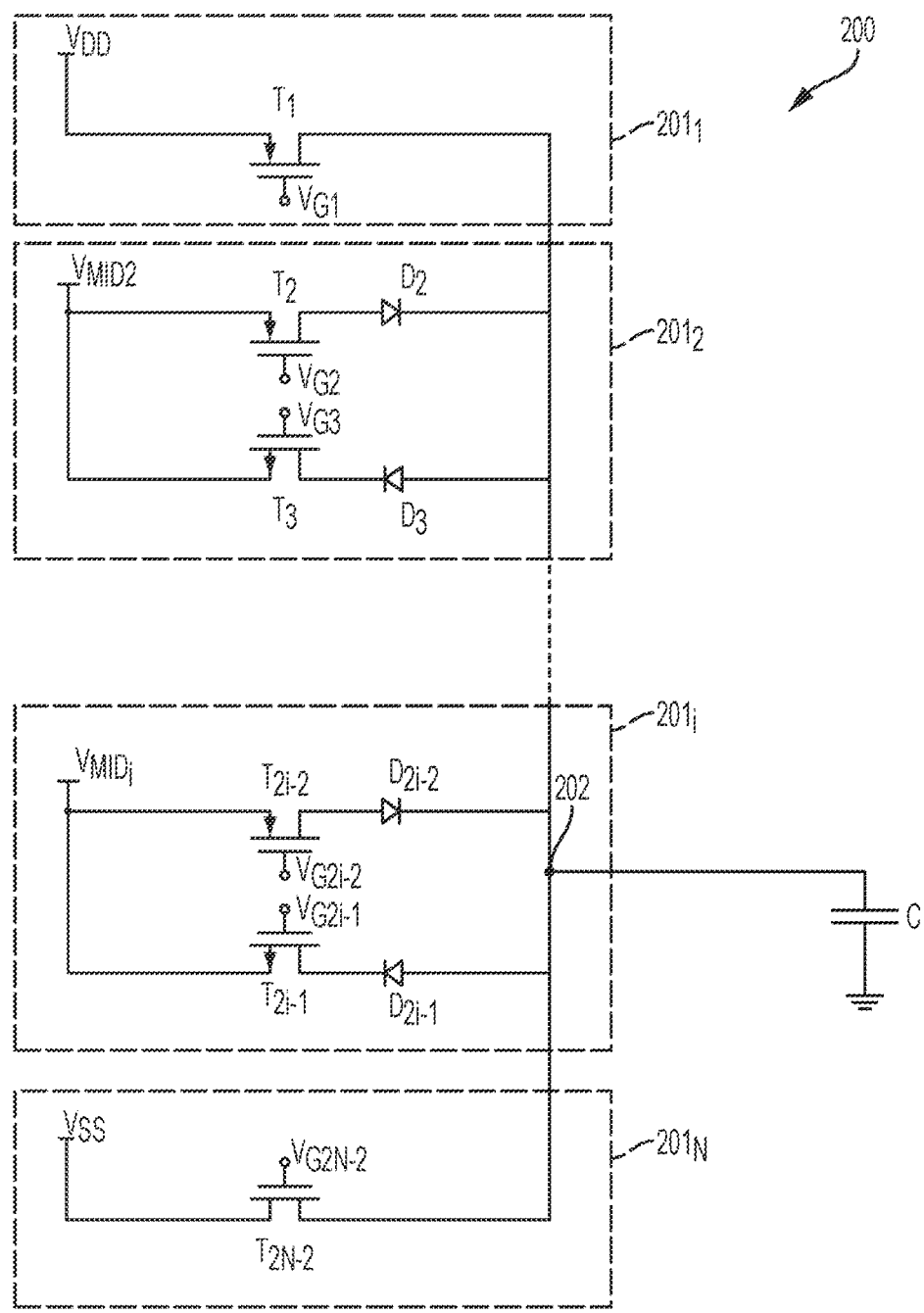
FIG. 2 illustrates a non-limiting circuit diagram of a multi-level pulser, according to a non-limiting embodiment of the present application.

FIG. 2 illustrates the circuit diagram of a multi-level pulser, according to aspects to the present application. In some embodiments, multi-level pulser 200 may be configured to transmit a pulse to capacitor C. Capacitor C may represent the capacitance associated with an ultrasound transducer. For example, capacitor C may represent a capacitive micromachined ultrasonic transducer (CMUT). However, multi-level pulser 200 may be configured to transmit a pulse to a resistor, a resistive network or a network exhibiting any suitable combination of resistive and reactive elements.

In the non-limiting embodiment illustrated in FIG. 2, multi-level pulser 200 is configured to provide an N-level pulse, where N may assume any value greater than 2. The power consumption $P_N$ associated with the transmission of a N-level pulser to capacitor C is equal to:

$$P_{(N)} = C*V^2*f/(N-1)$$

where f is the repetition frequency of the pulsed waveform. Accordingly, power consumption is reduced by a factor N−1 compared to typical 2-level pulsers.

In some embodiments, N-level pulser 200 may comprise 2N−2 transistors and 2N−4 diodes. However, any suitable number of transistors may be used. Among the 2N−2 transistors, N−1 may exhibit one type of conductivity and N−1 may exhibit the opposite type of conductivity. However any other suitable combination of types of conductivity may be used. For example, N−1 transistors may be nMOS and N−1 transistors may be pMOS. However any other suitable type of transistor may be used.

N-level pulser 200 may comprise N circuit blocks $201_1$, $201_2$ ... $201_N$. The N circuit blocks may be connected to node 202. One terminal of capacitor C may also be connected to node 202. The second terminal of capacitor C may be connected to ground. Circuit block $201_1$ may comprise pMOS transistor $T_1$, having the source connected to a reference voltage $V_{DD}$ and the drain connected to node 202. Reference voltage $V_{DD}$ may be a voltage supply. The gate of transistor $T_1$ may be driven by signal $V_{G1}$.

Circuit block $201_N$ may comprise nMOS transistor $T_{2N-2}$, having the source connected to a reference voltage $V_{SS}$ and the drain connected to node 202. In some embodiments, reference voltage $V_{SS}$ may be less than reference voltage $V_{DD}$. However, pulser 200 is not limited in this respect. Furthermore, reference voltage $V_{ss}$ may positive, negative or equal to zero. The gate of transistor $T_{2N-2}$ may be driven by signal $V_{G2N-2}$.

In some embodiments, circuit blocks $201_2$ may comprise two transistors $T_2$ and $T_3$ and two diodes $D_2$ and $D_3$. Transistor $T_2$ and diode $D_2$ may be connected in series and transistor $T_3$ and diode $D_3$ may also be connected in series. The two series may be connected in parallel. In some embodiments, $T_2$ may be a pMOS transistor, having the source connected to the reference voltage $V_{MID2}$ and the drain connected to the anode of $D_2$ and $T_3$ may be an nMOS transistor, having the source connected to $V_{MID2}$ and the drain connected to the cathode of $D_3$. In some embodiments, $V_{MID2}$ may be greater than $V_{SS}$ and less than $V_{DD}$. The cathode of $D_2$ and the anode of $D_3$ may be connected to node 202. Furthermore, the gate of $T_2$ may be driven by signal $V_{G2}$ and the gate of $T_3$ may be driven by signal $V_{G3}$.

In some embodiments, circuit blocks $201_i$, where i may assume any value between 3 and N−1, may comprise two transistors $T_{2i-2}$ and $T_{2i-1}$ and two diodes $D_{2i-2}$ and $D_{2i-1}$. Transistor $T_{2i-2}$ and diode $D_{2i-2}$ may be connected in series and transistor $T_{2i-1}$ and diode $D_{2i-1}$ may also be connected in series. The two series may be connected in parallel. In some embodiments, $T_{2i-2}$ may be a pMOS transistor, having the source connected to the reference voltage $V_{MIDi}$ and the drain connected to the anode of $D_{2i-2}$ and $T_{2i-1}$ may be an nMOS transistor, having the source connected to $V_{MIDi}$ and the drain connected to the cathode of $D_{2i-1}$. In some embodiments, $V_{MIDi}$ may be greater than $V_{SS}$ and less than $V_{MID2}$. The cathode of $D_{2i-2}$ and the anode of $D_{2i-1}$ may be connected to node 202. Furthermore, the gate of $T_{2i-2}$ may be driven by signal $V_{G2i-2}$ and the gate of $T_{2i-1}$ may be driven by signal $V_{G2i-1}$.

$V_{DD}$, $V_{SS}$ and $V_{MIDi}$, for any value of i, may have values between approximately −300V and 300V, between approximately −200V and 200V, or any suitable value or range of values. Other values are also possible.

Figure 3A:
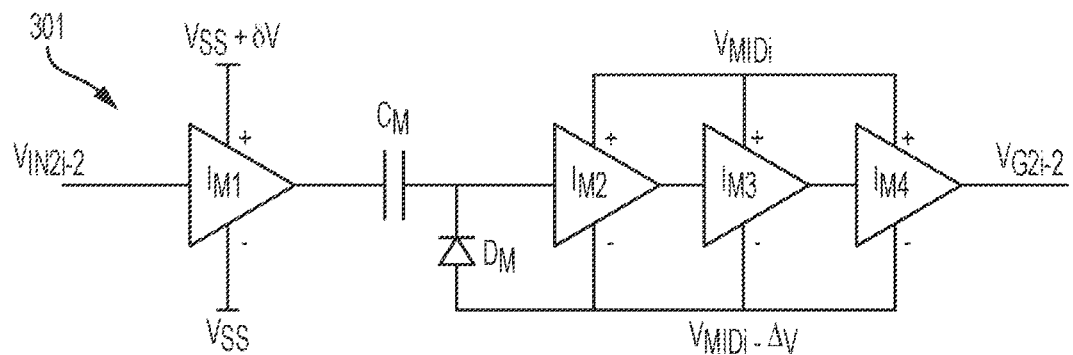
FIG. 3A illustrates a circuit diagram of a first embodiment of a level shifter, according to a non-limiting embodiment of the present application.
Figure 3B:
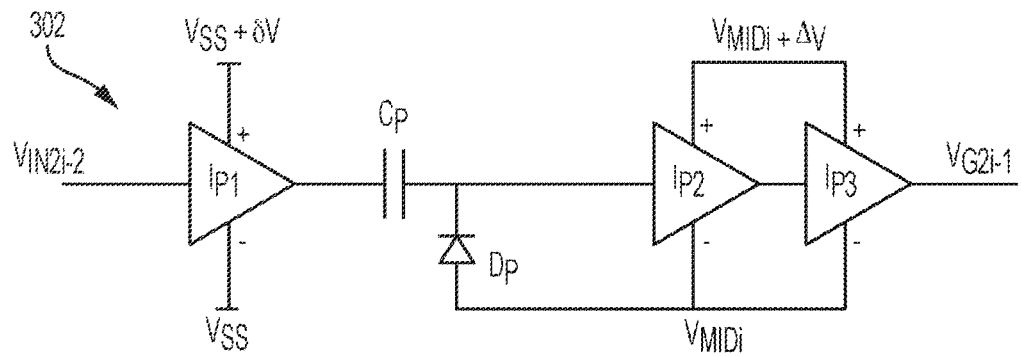
FIG. 3B illustrates a circuit diagram of a second embodiment of a level shifter, according to a non-limiting embodiment of the present application.

FIG. 3A and FIG. 3B illustrate two non-limiting embodiments of a level shifter circuit, according to aspects of the present application. In some embodiments, level shifter 301, shown in FIG. 3A, may be integrated on the same chip as pulser 200. In some embodiments, level shifter 301 may be used to drive any of the pMOS transistors of pulser 200. For example, level shifter 301 may be used to output signal $V_{G2i-2}$ to drive the gate of transistor $T_{2i-2}$. The input voltage $V_{IN2i-2}$ to level shifter 301 may be a control signal having two possible voltage levels: $V_{SS}$ and $V_{SS}+\delta V$, where $\delta V$ may assume any suitable value or range of values. In some embodiments, control signal $V_{IN2i-2}$ may be generated by a circuit integrated on the same chip as level shifter 301. However, control signal $V_{IN2i-2}$ may also be generated by a circuit integrated on a separate chip. In some embodiments, level shifter 301 may comprise an inverter $I_{M1}$, followed by capacitor $C_M$. The power supply pins of inverter $I_{M1}$ may be connected to voltages $V_{SS}$ and $V_{SS}+\delta V$. Capacitor $C_M$ may be followed by the series of a number of inverters. In some embodiments, capacitor $C_M$ is followed by three inverters $I_{M2}$, $I_{M3}$ and $I_{M4}$. The "−" and "+" power supply pins of inverter $I_{M2}$, $I_{M3}$ and $I_{M4}$ may be connected to voltages $V_{MIDi}-\Delta V$ and $V_{MIDi}$ respectively. In some non-limiting embodiments, level shifter 301 may comprise diode $D_M$. The cathode or diode $D_M$ may be connected to the output of capacitor $C_M$, while the anode may be connected to the $V_{MIDi}-\Delta V$ rail. While level shifter 301 comprises four inverters in the non-limiting embodiment of FIG. 3A, any suitable number of inverters may otherwise be used. Output voltage $V_{G2i-2}$ may assume two possible voltages: $V_{MIDi}-\Delta V$ and $V_{MIDi}$.

In some embodiments, level shifter 302, shown in FIG. 3B, may be integrated on the same chip as pulser 200. In some embodiments, level shifter 302 may be used to drive any of the nMOS transistors of pulser 200. For example, level shifter 302 may be used to output signal $V_{G2i-1}$ to drive the gate of transistor $T_{2i-1}$. The input voltage $V_{IN2i-1}$ to level shifter 302 may be a control signal having two possible voltage levels: $V_{SS}$ and $V_{SS}+\delta V$. In some embodiments, control signal $V_{IN2i-1}$ may be generated by a circuit integrated on the same chip as level shifter 302. However, control signal $V_{IN2i-1}$ may also be generated by a circuit integrated on a separate chip. In some embodiments, level shifter 302 may comprise an inverter $I_{P1}$, followed by capacitor $C_P$. The power supply pins of inverter $I_{P1}$ may be connected to voltages $V_{SS}$ and $V_{SS}+\delta V$. Capacitor $C_P$ may be followed by the series of a number of inverters. In some embodiments, capacitor $C_P$ is followed by two inverters $I_{P2}$ and $I_{P3}$ The power supply pins of inverter $I_{M2}$ and $I_{M3}$ may be connected to voltages $V_{MIDi}$ and $V_{MIDi}+\Delta V$. In some non-limiting embodiments, level shifter 302 may comprise diode DP. The cathode or diode $D_P$ may be connected to the output of capacitor $C_P$, while the anode may be connected to the $V_{MIDi}$ rail. While level shifter 302 comprises three inverters in the non-limiting embodiment of FIG. 3B, any suitable number of inverters may otherwise be used. Output voltage $V_{G2i-1}$ may assume two possible voltages: $V_{MIDi}$ and $V_{MIDi}+\Delta V$.

According to aspects of the present application, level shifters 301 and 302 may dissipate power only when a level is switched, while static power may be negligible. Capacitors $C_M$ and $C_P$ may be used to shift the voltage level by storing a constant voltage drop across them. For example, the static power consumption may be less than 100mW, less than 1mW, less than 1 µW or less than any suitable value.

FIG. 4A, FIG. 4B, FIG. 4C, FIG. 4D, FIG. 4E, and FIG. 4F illustrate six snapshots of pulser 200 corresponding to the six phases associated with the formation of a 4-level pulse, according to aspects on the present application. In the figures, only the active blocks are shown. While in the non-limiting example N is equal to 4, any other suitable value of N, such that N is greater than 2, may otherwise be used. In the example, $V_{SS}$ is set to 0.

Figure 4A:
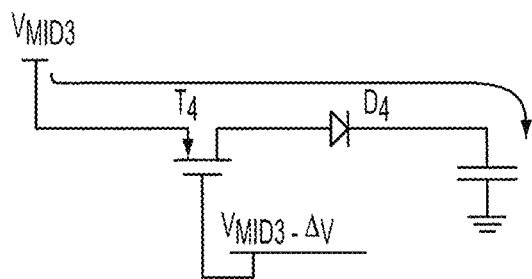
FIG. 4A illustrates a non-limiting equivalent circuit of the circuit of FIG. 2, during a first phase of a multi-level pulse formation, according to a non-limiting embodiment of the present application.
Figure 5:
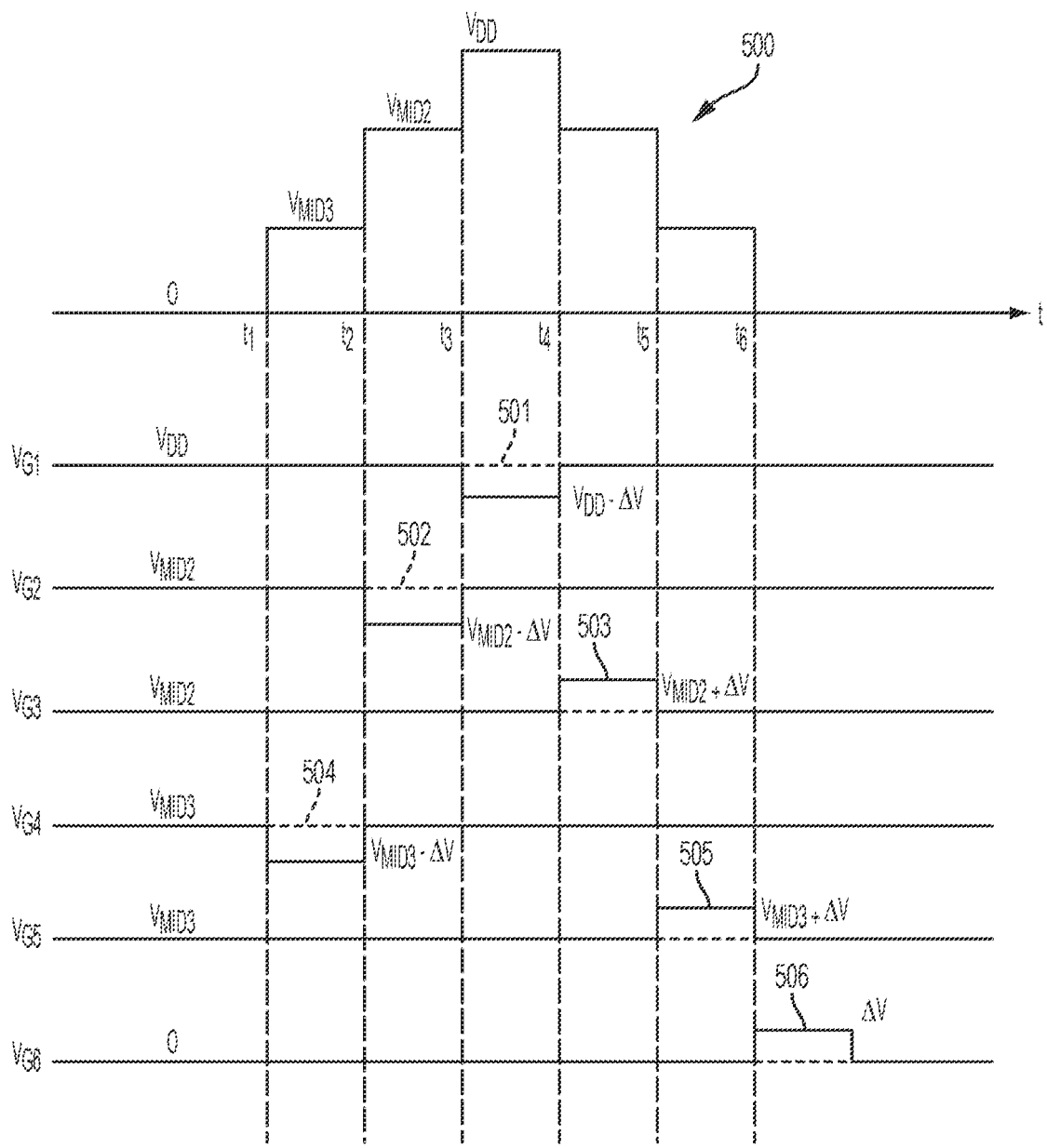
FIG. 5 is a graph illustrating a non-limiting example of a time-dependent multi-level pulse and the control signals, according to a non-limiting embodiment of the present application.

FIG. 5 illustrates a non-limiting example of multi-level pulse 500 generated according to aspects of the present application. In the non-limiting example, pulse 500 exhibits 4 levels: 0, $V_{MID3}$, $V_{MID2}$, and $V_{DD}$. In addition, FIG. 5 illustrates the 6 control signals $V_{G1}$, $V_{G2}$, $V_{G3}$, $V_{G4}$, $V_{G5}$, and $V_{G6}$ used to respectively drive the gates of transistors $T_1$, $T_2$, $T_3$, $T_4$, $T_5$, and $T_6$. The process associated with the pulse generation can be divided in 6 phases. Between $t_1$ and $t_2$, pulse 500 may be increased from 0 to $V_{MID3}$ by providing a negative pulse 504 to transistor $T_4$ through $V_{G4}$ as shown in FIG. 5. FIG. 4A illustrates pulser 201 between $t_1$ and $t_2$. During this period, the gate of transistor $T_4$ may be driven by a voltage equal to $V_{MID3}-\Delta V$. $\Delta V$ may be chosen so as to create a conductive channel and cause transistor $T_4$ to drive a current between the source and the drain passing through diode $D_4$. Such current may charge capacitor C, such that an output voltage of $V_{MID3}$ is obtained, neglecting any voltage drop on $T_4$ and $D_4$. Pulse 504 may be obtained through level shifter 301.

Figure 4D:
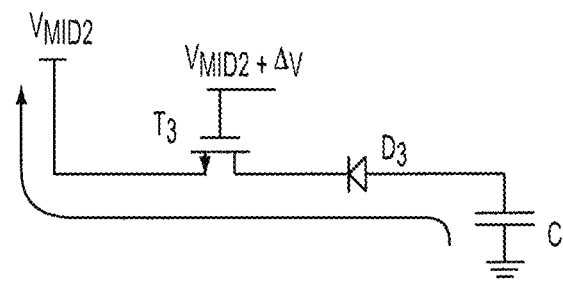
FIG. 4D illustrates a non-limiting equivalent circuit of the circuit of FIG. 2, during a fourth phase of a multi-level pulse formation, according to a non-limiting embodiment of the present application.
Figure 4B:
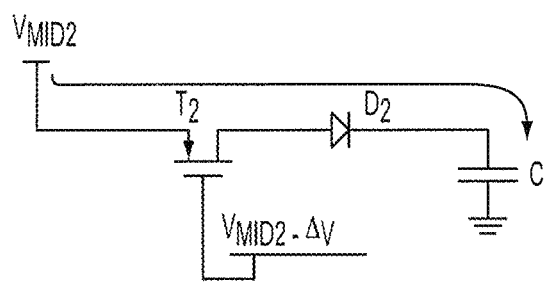
FIG. 4B illustrates a non-limiting equivalent circuit of the circuit of FIG. 2, during a second phase of a multi-level pulse formation, according to a non-limiting embodiment of the present application.

Between $t_2$ and $t_3$, pulse 500 may be increased from $V_{MID3}$ to $V_{MID2}$ by providing a negative pulse 502 to transistor $T_2$ through $V_{G2}$ as shown in FIG. 5. FIG. 4B illustrates pulser 201 between $t_2$ and $t_3$. During this period, the gate of transistor $T_2$ may be driven by a voltage equal to $V_{MID2}-\Delta V$. $\Delta V$ may be chosen so as to create a conductive channel and cause transistor $T_2$ to drive a current between the source and the drain passing through diode $D_2$. Such current may charge capacitor C, such that an output voltage of $V_{MID2}$ is obtained, neglecting any voltage drop on $T_2$ and $D_2$. Pulse 502 may be obtained through level shifter 301.

Figure 4E:
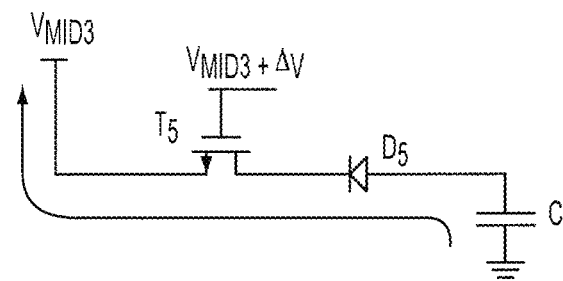
FIG. 4E illustrates a non-limiting equivalent circuit of the circuit of FIG. 2, during a fifth phase of a multi-level pulse formation, according to a non-limiting embodiment of the present application.
Figure 4C:
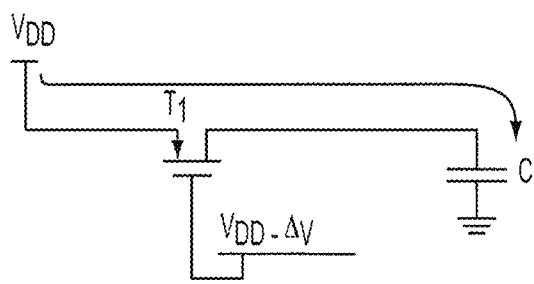
FIG. 4C illustrates a non-limiting equivalent circuit of the circuit of FIG. 2, during a third phase of a multi-level pulse formation, according to a non-limiting embodiment of the present application.

Between $t_3$ and $t_4$, pulse 500 may be increased from $V_{MID2}$ to $V_{DD}$ by providing a negative pulse 501 to transistor $T_1$ through $V_{G1}$ as shown in FIG. 5. FIG. 4C illustrates pulser 201 between $t_3$ and $t_4$. During this period, the gate of transistor $T_1$ may be driven by a voltage equal to $V_{DD}-\Delta V$. $\Delta V$ may be chosen so as to create a conductive channel and cause transistor $T_1$ to drive a current between the source and the drain. Such current may charge capacitor C, such that an output voltage of $V_{DD}$ is obtained, neglecting any voltage drop on $T_1$. Pulse 501 may be obtained through level shifter 301.

Between $t_4$ and $t_5$, pulse 500 may be decreased from $V_{DD}$ to $V_{MID2}$ by providing a positive pulse 503 to transistor $T_3$ through $V_{G3}$ as shown in FIG. 5. FIG. 4D illustrates pulser 201 between $t_4$ and $t_5$. During this period, the gate of transistor $T_3$ may be driven by a voltage equal to $V_{MID2}+\Delta V$. $\Delta V$ may be chosen so as to create a conductive channel and cause transistor $T_3$ to drive a current between the drain and the source. Such current may discharge capacitor C, such that an output voltage of $V_{MID2}$ is obtained, neglecting any voltage drop on $T_3$ and $D_3$. Pulse 503 may be obtained through level shifter 302.

Between $t_5$ and $t_6$, pulse 500 may be decreased from $V_{MID2}$ to $V_{MID3}$ by providing a positive pulse 505 to transistor $T_5$ through $V_{G5}$ as shown in FIG. 5. FIG. 4E illustrates pulser 201 between $t_5$ and $t_6$. During this period, the gate of transistor $T_5$ may be driven by a voltage equal to $V_{MID3}+\Delta V$. $\Delta V$ may be chosen so as to create a conductive channel and cause transistor $T_5$ to drive a current between the drain and the source. Such current may discharge capacitor C, such that an output voltage of $V_{MID3}$ is obtained, neglecting any voltage drop on $T_5$ and $D_5$. Pulse 505 may be obtained through level shifter 302.

Figure 4F:
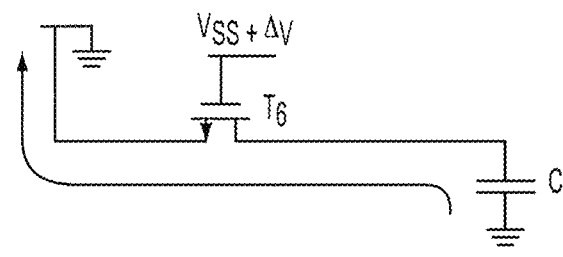
FIG. 4F illustrates a non-limiting equivalent circuit of the circuit of FIG. 2, during a sixth phase of a multi-level pulse formation, according to a non-limiting embodiment of the present application.

After $t_6$, pulse 500 may be decreased from $V_{MID3}$ to 0 by providing a positive pulse 506 to transistor $T_6$ through $V_{G6}$ as shown in FIG. 5. FIG. 4F illustrates pulser 201 after $t_6$. During this period, the gate of transistor $T_6$ may be driven by a voltage equal to $\Delta V$. $\Delta V$ may be chosen so as to create a conductive channel and cause transistor $T_6$ to drive a current between the drain and the source. Such current may discharge capacitor C, such that an output voltage of 0 is obtained, neglecting any voltage drop on $T_6$. Pulse 506 may be obtained through level shifter 302.

In the non-limiting example in connection to FIG. 5, pulse 500 is unipolar. However, multi-level pulser 200 in not limited in this respect. Multi-level pulser 200 may alternatively be configured to transmit bipolar pulses exhibiting levels having positive and negative voltages. In accordance with another aspect of the present application, the multi-level pulser 200 may be considered a multi-level charge recycling waveform generator in that charge recycling occurs on the decrementing step as charge is transferred from the output capacitance back into the power supply. In accordance with another aspect of the present application, although the multi-level pulser has been described as being used to drive a capacitive output, it may also be used to drive a resistive output.

The amount of power saving when using a level shifter of the types described herein may be significant. In some embodiments, utilizing a level shifter of the types described herein may provide substantial power saving by setting the static power consumption to approximately zero. Accordingly, power may be dissipated only during switching states.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus for an ultrasound device, comprising:
a level shifter comprising:
   a level shifter input terminal to receive an input voltage;
   a level shifter output terminal to provide an output voltage level-shifted from the input voltage;
   circuitry coupled between the level shifter input terminal and the level shifter output terminal, the circuitry comprising:
      a first inverter having a first inverter input terminal and a first inverter output terminal;
      a capacitor having a first terminal and a second terminal;
      a diode having an anode and a cathode; and
      a series of at least second and third inverters, each of the second and third inverters having a power connection, the second inverter having a second inverter input terminal and a second inverter output terminal, and the third inverter having a third inverter input terminal and a third inverter output terminal;
   wherein:
      the first inverter input terminal is or is coupled to the level shifter input terminal;
      the first inverter output terminal is coupled to the first terminal of the capacitor;
      the second terminal of the capacitor is coupled to the second inverter input terminal;
      the anode of the diode is coupled to the power connection;
      the cathode of the diode is coupled to the second terminal of the capacitor; and
      the third inverter output terminal is or is coupled to the level shifter output terminal.

2. The apparatus of claim 1, wherein:
the first inverter comprises a positive power supply connection coupled to a first voltage and a negative power supply connection coupled to a second voltage; and
the level shifter is configured to receive either of the first voltage or the second voltage as the input voltage.

3. The apparatus of claim 1, wherein:
each of the second and third inverters comprises a positive power supply connection coupled to a first voltage and a negative power supply connection coupled to a second voltage; and
the level shifter is configured to output, as the output voltage, a voltage that is either the first voltage or the second voltage.

4. The apparatus of claim 3, wherein the first voltage and/or the second voltage is substantially between approximately −300 V and 300 V.

5. The apparatus of claim 1, wherein:
each of the second and third inverters comprises a positive power supply connection coupled to a first voltage and a negative power supply connection coupled to a second voltage; and
the anode of the diode is coupled to the second voltage.

6. The apparatus of claim 1, further comprising:
a pulser having a pulser input terminal and a pulser output terminal; and
an ultrasonic transducer having an ultrasonic transducer input terminal;
wherein:
   the level shifter output terminal is coupled to the pulser input terminal; and
   the pulser output terminal is coupled to the ultrasonic transducer input terminal.

7. The apparatus of claim 6, wherein:
the pulser comprises a p-type metal-oxide-semiconductor field-effect transistor (pMOSFET); and
the series of two or more second inverters comprises an odd number of inverters.

8. The apparatus of claim 6, wherein:
the pulser comprises a n-type metal-oxide-semiconductor field-effect transistor (nMOSFET); and
the series of two or more second inverters comprises an even number of inverters.

9. The apparatus of claim 6, wherein the level shifter, the pulser, and the ultrasonic transducer are monolithically integrated on a single substrate.

10. The apparatus of claim 1, wherein:
the first inverter input terminal is coupled to the level shifter input terminal; and
the third inverter output terminal is coupled to the level shifter output terminal.

* * * * *